United States Patent [19]

Linden et al.

[11] Patent Number: 5,567,685
[45] Date of Patent: Oct. 22, 1996

[54] WATER-SOLUBLE POLYENE CONJUGATE

[75] Inventors: Galina Linden, Rishon LeZion; Abraham J. Domb, Efrat; Itzhack Polacheck; Shimon Benita, both of Jerusalem, all of Israel

[73] Assignee: Yissum Research Development Company of the Hebrew University of Jerusalem, Jerusalem, Israel

[21] Appl. No.: 291,292

[22] Filed: Aug. 16, 1994

[51] Int. Cl.$^6$ .............................. A61K 31/70; C07H 1/06; C07G 11/00; C08B 37/02

[52] U.S. Cl. ............................. 514/31; 514/54; 514/59; 536/6.5; 536/1.11; 536/112; 536/123; 536/123.1; 536/124; 536/127

[58] Field of Search .................................. 536/1.11, 112, 536/123.1, 124, 127, 6.5; 424/133.1, 130.1; 514/31, 54, 59

[56] References Cited

U.S. PATENT DOCUMENTS

| | | | |
|---|---|---|---|
| 4,446,316 | 5/1984 | Chazov et al. | 536/112 |
| 4,707,471 | 11/1987 | Laum | 536/123 |
| 5,059,685 | 10/1991 | Conti | 536/123.1 |
| 5,177,059 | 1/1993 | Handley et al. | 514/8 |
| 5,332,567 | 7/1994 | Goldenberg | 424/1.49 |

FOREIGN PATENT DOCUMENTS

| | | |
|---|---|---|
| 3032606 | 1/1984 | Germany. |
| 61-64701 | of 1986 | Japan. |
| 809105 | 2/1959 | United Kingdom. |
| 844289 | 9/1960 | United Kingdom. |
| 978170 | 12/1994 | United Kingdom. |
| 93/25239 | 12/1993 | WIPO. |
| 9512620 | 5/1995 | WIPO. |

OTHER PUBLICATIONS

R. Mehta et al., "Liposomal Amphotericin B is Toxic to Fungal Cells But Not to Mammalian Cells", BBA Report, 1984, pp. 230–234.

M. Maddux et al., "A Review of Complications of Amphotericin–B Therapy: Recommendations for Prevention and Management", Drug Intelligence and Clinical Pharmacy, vol. 14, Mar. '80, pp. 177–181.

R. Mehta et al., "Formulation Toxicity, and Antifungal Activity In Vitro of Liposome–Encapsulated Nystatin as Therapeutic Agent for Systemic Candidiasis", Antimicrob. Agents Chemero., Dec. 1987, pp. 1897–1900, vol. 31, No. 12.

M. DeGregorio et al., "Candida Infections in Patents with Acute Leukemia: Ineffectiveness of Nystatin Prophylaxis and Relationship Between Oropharyngeal and Systemic Candidiasis", Amer. Cancer Soc., Dec. 1982, vol. 50, pp. 2780–2784.

C. Larsen, "Physicochemical and chemical aspects in relation to in vivo properties", Dextran Prodrligs, pp. 1–233, (1990).

F. Levi–Schaffer et al., "Reduced Toxicity of Daunorubicin by Conjugation to Dextran", Cancer Treat. Rep. vol. 66, No. 1, Jan. '82, pp. 107–114.

(List continued on next page.)

Primary Examiner—John Kight, III
Assistant Examiner—Everett White
Attorney, Agent, or Firm—Helfgott & Karas, P.C.

[57] ABSTRACT

A method for producing a substantially stable water-soluble polysaccharide conjugate of a polyene antibiotic is described. The method comprises the following steps: (a) activating the polysaccharide to a dialdehyde by periodate oxidation; (b) purifying the dialdehyde from interfering anions and by-products; (c) coupling the polyene to the purified dialdehyde by Schiff base formation to form the conjugate; and (d) purifying the conjugate. In a preferred embodiment, the conjugate of step (c) is reduced to an amine conjugate by a reducing agent prior to purification. Also described are imine and amine polysaccharide conjugates of the polyene Nystatin.

20 Claims, 12 Drawing Sheets

OTHER PUBLICATIONS

A. Bernstein et al., "Higher Antitumor Efficacy of Daunomycin When Linked to Dextran: In Vivo and In Vitro Studies", J. Natl. Cancer Inst., vol. 60, No. 2, Feb. '78, pp. 379–384.

S. L. Law et al., "The Leakage Characteristics of Liposome–Encapsulated Adriamycin–Dextran Conjugates", Drug Dev. and Indus. Phar. vol. 14, No. 1, 1988, pp. 143–153.

K. P. Khomyakov et al., "Synthesis of Polymeric Druvs from Dextran Derivative Synthesis of polymeric drugs", pp. 1145–1151, (1965).

E. Hurwitz et al., "Soluble Macromolecules as Carriers for Daunorubicin", Journal of App. Biochem., vol. 2, 1980, pp. 25–35.

I. Polacheck et al., "Activity of Compound G2 Isolated from Alfalfa Roots against Medically Important Yeasts", Antimicrobial Agents Chemo., Aug. '86, vol. 30, No. 2, pp. 290–294.

G. Lindenbaum et al., J. Khim–Pharm. 1977, vol. 11, No. 6, pp. 80–83.

G. Lindenbaum et al., Prikl. Biochim. Mikrobiol. 1982, vol. 18, No. 2, pp. 212–220 (Russ).

G. Michel, "Nystatin", Analytical Profiles of Drug Substances, No. 6, pp. 341–421, 1977.

Bucklin et al., Therapeutic Efficacy of a Polymyxin B–Dextran 70 Conjugate in Experimental Model of Endotoxemia, Jul. 1995, pp. 1462–1466.

Mocanu et al., Macromolecular Drug Conjugates II. Metronidaz Dextran Prodrugs, Oct. 1993, pp. 383–392.

Cera et al., Anthracycline Antiotics Supported On Water Soluable Polysaccharides: Synthesis and physicochemical characterization, Apr. 1988, pp. 66–74.

Manabe et al., Production of a Monoclonal Antibody–Mitomycin Conjugate, Utilizing Dextran T–40, and its Biological Activit Mar. 1994, pp. 289–291.

WATER-SOLUBLE POLYENE CONJUGATE

FIELD OF THE INVENTION

The present invention relates to a method for preparing water-soluble polysaccharide conjugates of polyene antibiotics and, more particularly, to conjugates of the antifungal polyenes nystatin and amphotericin B. The invention also relates to conjugates prepared by the method and pharmaceutical compositions comprising them.

BACKGROUND OF THE INVENTION

The treatment of fungal infections remains a major problem in spite of the availability of effective antifungal drugs such as polyenes. The clinical use of these commercial drugs is continuously growing as a result of the increasing incidence of life-threatening fungal infections, particularly in immunocompromised hosts such as cancer patients, patients after transplantation and AIDS patients. However, most of the available polyene antibiotics are toxic and cause side effects that limit their clinical application. The most widely-used polyene antibiotics are amphotericin B (Amph B) and nystatin (Nys)—the drugs of choice for the treatment of mycotic infections caused by a wide range of fungi. The first exists as a parenteral drug in a solubilized form, Fungizone®, and in the more recently developed, less toxic liposomal form, Ambisome®. However, major technical difficulties associated with the physical stability of liposomes and liposome batch-to-batch reproducibility still need to be overcome in order to allow for a more realistic development of liposomal pharmaceutical intravenous forms of antifungals [1,2]. Although Fungizone® does not contain liposomes, its therapeutic dose is very close to its maximal tolerated dose (MTD), so that it is usually prescribed only in life-threatening situations. With respect to Nys, the problem of the development of new effective parenteral antifungal drug forms still remains. Although liposomal forms of Nys have been described in the literature [3], these suffer from problems of drug leakage from liposomes and maintenance of drug chemical integrity, in addition to the problems mentioned above with respect to Amph B. The usage of Nys is therefore currently limited to oral or topical forms, and no parenteral formulations have as yet been developed for this potent drug [4].

Water soluble, oxidized polysaccharides such as, for example, dextrans are considered to be one of the most attractive drug carrier candidates [5]. Dialdehydedextran (DAD), the main product of the oxidation reaction of periodate with dextran, has been proposed as a stabilizer for enzymes (e.g. U.S. Pat. No. 4,446,316) and drugs, including antibiotics [6-10]. However, no conjugates of polyene antibiotics applicable for parenteral administration have been reported.

GB 978,170 describes a process for the preparation of water-soluble imine derivatives of polyene antibiotics, in which the polysaccharide is oxidized to a polydialdehyde prior to being reacted with the polyene. Among the conjugates described in the above patent are pimaricin-dextran and Nys-corn starch. No amine conjugates are described in the British patent. In experiments carried out by the applicant of the present application, and described in Example 8, it was found that although a Nys-dextran conjugate prepared according to the process described in the above patent is water-soluble, it has very low stability and activity, and is susceptible to drastic degradation of the polymer and inactivation of the conjugated drug. It is believed that this is due to the fact that the oxidized polymer is not purified from excess oxidizing agent prior to conjugation, thus resulting in the polyene undergoing oxidation. This purification is essential for the stability, efficacy and lack of toxicity of the conjugated drug, as will be further described below.

In summary, none of the above studies succeed in documenting a beneficial effect of Nys administration in water-soluble form against systemic fungal infections. Hence, the formation of an IV-injectable, non-toxic system for polyenes in general and Nys in particular remains a problem which limits their use for systemic treatment of serious fungal diseases.

SUMMARY OF THE INVENTION

It is an object of the present invention to provide a method for the preparation of water-soluble polyene antibiotics which are suitable for intravenous administration.

It is a further object of the present invention to provide water-soluble conjugates of polyene antibiotics having higher stability, greater efficacy and lower toxicity than those of the free polyene.

Additionally, it is an object of the present invention to provide a pharmaceutical composition comprising a water-soluble polyene antibiotic which is suitable for intravenous administration as well as for topical application.

According to one aspect of the present invention, there is provided a method for producing a substantially stable water-soluble polysaccharide conjugate of a polyene antibiotic comprising:

(1) activating said polysaccharide to a dialdehyde by periodate oxidation;

(2) purifying said dialdehyde from interfering anions and by-products;

(3) coupling said polyene to said purified dialdehyde by Schiff base formation to form said conjugate; and (4) purifying said conjugate.

According to a second aspect of the present invention, there is provided a method for producing a substantially stable water-soluble polysaccharide conjugate of a polyene antibiotic comprising:

(1) activating said polysaccharide to a dialdehyde by periodate oxidation;

(2) purifying said dialdehyde from interfering anions and by-products;

(3) coupling said polyene to said purified dialdehyde by Schiff base formation to form said conjugate;

(4) reducing said conjugate to an amine conjugate by a reducing agent; and (5) purifying said conjugate.

In preferred embodiments of the present invention, the polyene is Nys or Amph B and the polysaccharide is dextran or arabinogalactan.

According to another aspect of the present invention, there is provided a substantially stable, water-soluble conjugate of a polysaccharide and a polyene antibiotic.

In a preferred embodiment, the polyene is conjugated to the polysaccharide via an amine bond.

According to yet another aspect of the present invention, there is provided a pharmaceutical composition for use in the treatment of fungal infections comprising the conjugate of the invention.

The reaction of periodate with a polysaccharide (structure A, FIG. 1) leading to an oxidized polysaccharide (OP— structure B) is well-studied, and technological conditions are proposed for highly effective separation of the activated polymer from the interfering anions (periodate, iodate and formate) of the reaction mixture. This is achieved by applying the reaction mixture to a column filled with a strongly basic anion-exchanger in the acetate form. This process of purification is fast and provides a high yield of the purified OP at the initial concentration, the anion-exchanger being easily regenerated afterwards. Similar methods were successfully used in the coupling of a number of proteins to DAD [13-15], but no attempt was made to prepare such a carrier for conjugation of antibiotics or other low-molecular weight drugs.

Figure 1:
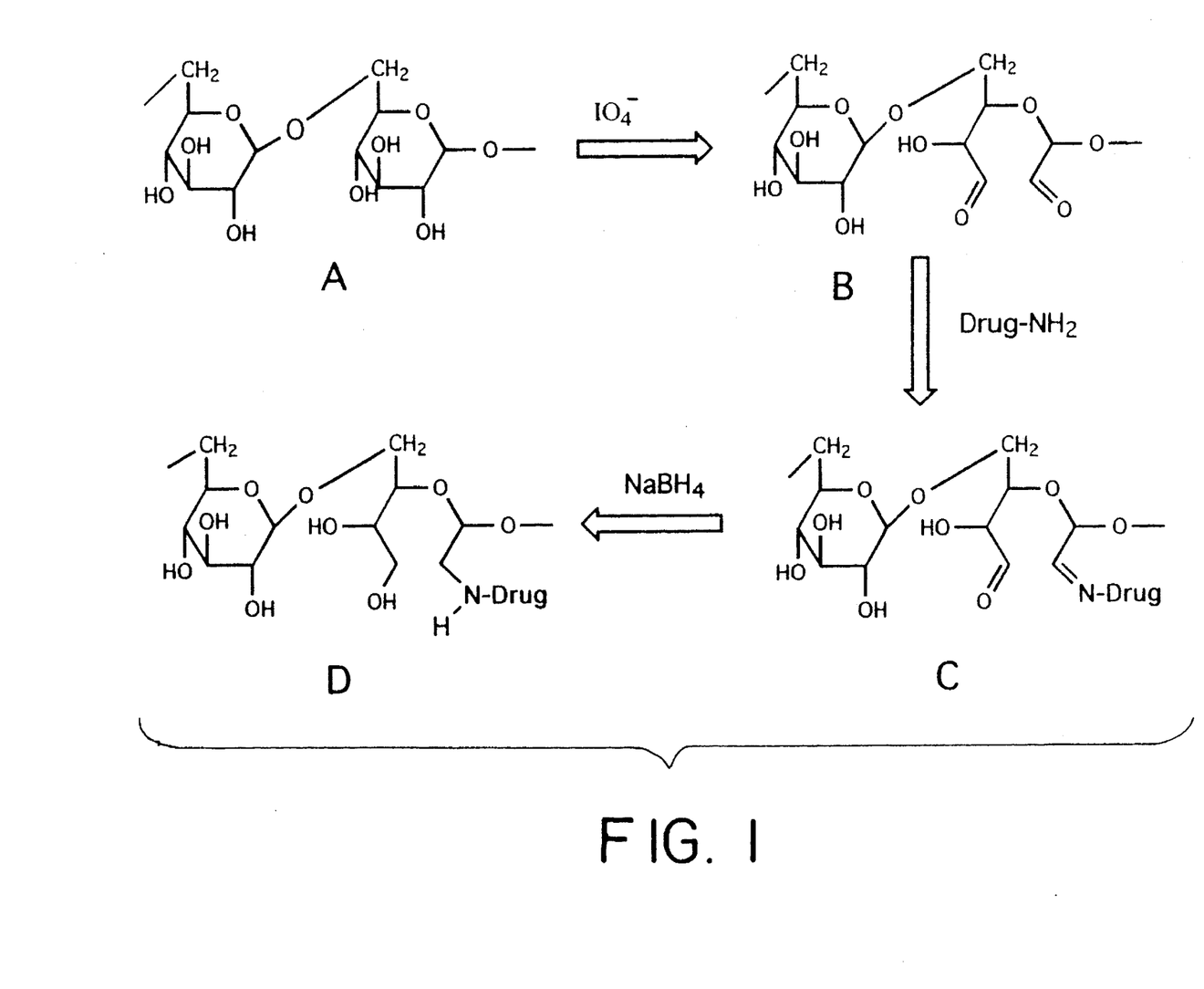
FIG. 1 illustrates the reaction scheme of a preferred embodiment of the method of the invention.

The OP is then reacted with the amino group of a polyene antibiotic to form a Schiff base (structure C). Preferably, the Schiff base bond is then converted into a stable amine bond by a reducing agent, preferably sodium or potassium borohydride (structure D). Such a bond is unlikely to be easily hydrolyzed in the body. It is to be understood that other reducing agents, such as $NaHSO_3$ or $HO-NH_2:HCl$, can also be used.

The conjugate is then separated from the salts, low molecular weight polymer fractions and traces of unbound water-soluble drug by dialysis, followed by centrifugation and lyophilization.

The conjugates do not contribute markedly to an increase in osmotic pressure, as expected. Therefore for the preparation of an intravenous solution, the lyophilized conjugate is simply dissolved in saline and sterilized by filtration or autoclave.

If it is desired to prepare eye or ear drops, appropriate preservatives such as parahydroxybenzoate ester derivatives (methyl, propyl, butyl) should be added to the saline solution.

BRIEF DESCRIPTION OF THE DRAWINGS

The present invention will be better understood from the following detailed description of preferred embodiments, taken in conjunction with the following drawings in which.

DETAILED DESCRIPTION OF PREFERRED EMBODIMENTS

Methods

1. Chromatography

HPLC-GPC was performed on a Bio-Sil R SEC-125 HPLC Gel Filtration Column 300×7.5 mm (Japan), using DDW as the mobile phase.

GPC was performed on a column containing a total volume of 55 ml of Sephadex G-75 and a void volume of 19 ml using DDW as an eluent.

2. Spectral Methods

UV spectra were recorded using a UVIKON Spectrophotometer (Kontron Instruments).

IR spectra were recorded using a Perkin-Elmer System 2000 FT-IR.

3. Sterilization and Lyophilization of Conjugates

Sterile antifungal conjugates for the animal studies were prepared by filtration through sterile pyrogen-free filters (0.2 Micron, 20 mm, 45 mm, Schleicher & Schuell, Dassel, Germany). Lyophilization was performed in a Christ Alpha-Is Lyophilizer, Germany. The sterility was validated by a sterility test using a Bactec 46 apparatus (Johnson Laboratories, Towson, Md., USA). This instrument is designed to measure radioactive carbon dioxide quantitatively in Bactec cultural vials inoculated with sample tests. The detection of $^{14}CO_2$ above a given baseline level in culturing aerobic or anaerobic vials indicates the presence of viable microorganisms in the original inoculum.

4. Toxicity Studies a. In vitro studies

Assay of toxicity to human erythrocytes was performed by following the release of hemoglobin at 550 nm in the course of a hemolysis reaction as described (1,3) at predetermined time intervals over a period of up to 70 hours.

b. In vivo studies

Healthy male albino BALB/c mice weighing 20 g were injected through the tail vein with various doses of Nys forms (0.5 and 1.0 mg/kg). Each dosage form was administered i.v. by single-bolus injections of 0.10 or 0.20 ml of solution, prepared using sterile water, to groups of 10 mice. Survival was followed for up to 45 days. In the case of multiple dose treatment, five consecutive daily doses of Nys conjugate solution (0.1 ml) were injected into the tail veins of the mice (groups of 10).

5. Efficacy Studies a. In vitro study of bioactivity against Candida

The yeast susceptibility test (MIC determination) was used [12]. The MIC (minimal inhibitory concentration) values of Nys and its conjugates with DAD were determined against *Candida albicans* CBS 562 (reference type strain) according to the agar dilution method using yeast Nitrogen Base Medium (Difco) and four serial dilutions.

b. In vivo study of bioactivity against Candida and Cryptococosis

In all the experiments, *C. albicans* CBS 562 were injected into the tail vein of male albino BALB/c mice (20±3 g) by a single bolus of 0.1 ml solution. The inocula ranged from $5 \times 10^4$ to $10^5$ yeast cells per mouse from a 24 hr culture on Sabouraud Dextrose Agar at 37° C. With these inocula, systemic infections are regularly produced in mice causing total killing within 10–15 days. The appropriate inoculum for each experiment was empirically determined. Yeast concentration was determined by hematocytometer count. Viable count was measured as colony forming units (CFU) on Sabouraud Dextrose agar after 2 days of incubation at 37° C. In some experiments, in addition to the mortality, multiplication in the kidneys as measured by CFU of homogenized organs was also monitored.

Mice infected as described above were treated with Nys solution at the maximal tolerated dose for intact mice—1 mg/kg in 2% DMSO (the solvent in such concentration was shown to be non-toxic) or with Nys-conjugate. 10 mice were used in each treatment and maintained in separate cages. Treatment began 24 h after the initiation of infection by injection of five consecutive daily doses of Nys or Nys conjugate with a dose equal to 25 mg Nys/kg in the multi-treatment experiment, or a single bolus of the conjugate at a concentration equal to 80 mg/kg (0.1 ml) in the single-treatment experiment. For comparison, taking into account the prolongation effect of the conjugate, another group of mice got a multiple twice-a-week IV treatment (5 injections with an interval of 2–3 days between injections) of Nys or the conjugate at the above mentioned doses. A control group of 10 infected mice treated with saline instead of the conjugate was included. The number of surviving animals in each group was recorded daily over a period of up to 45 days.

The efficacy study was carried out for a cryptococceses model under similar experimental conditions.

EXAMPLES

Example 1—formation of Schiff base conjugate 1.0 g of Dextran-40 (average M.W. 40,000, Sigma) was dissolved in 20.0 ml of distilled water after stirring at room temperature for 5 mins. 1.275 g of potassium periodate (Aldrich Chem. Co.) was added and the mixture was effectively stirred at the same conditions for 2 hours until the salt dissolved entirely. The formed dialdehyde dextran (DAD) was separated from the interfering anions and byproducts of the reaction mixture by applying it to a column (6 mm×80 mm, Vo=2.0 ml) filled with Dowex-1 in the acetate form, obtained by the pre-treatment of the commercial anion exchanger (Sigma) with a 1M acetic acid solution. The purified DAD was at an initial concentration of 50.0 mg/ml and was 50% oxidized as determined by the iodometric method[12].

Figure 2:
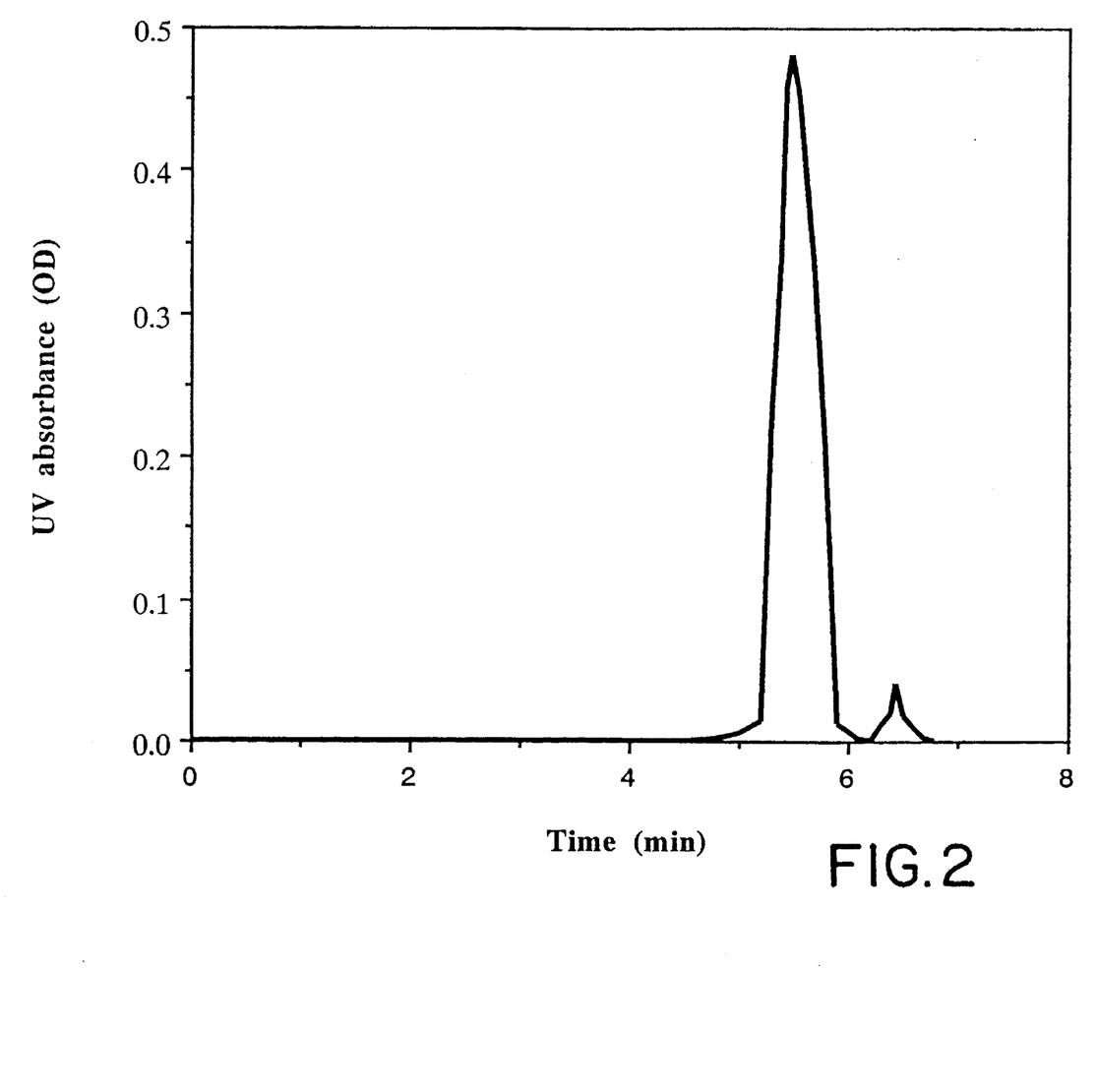
FIG. 2 illustrates an HPLC analysis of a conjugate product of a preferred embodiment of the method of the invention.

20.0 ml of the purified DAD solution were mixed with an equal volume of 0.2M borate buffer solution pH 9.1 and 400.0 mg of Nys was added to the polymer solution (initial concentrations of polymer and drug were 25 mg/ml and 20 mg/ml, respectively). The pH value of the mixture was maintained at 8.9±0.1 for 16 hours at 37° C. At the end of that time, all the Nys was dissolved, and this fact together with the existence of a single peak in the HPLC analysis (FIG. 2) of the reaction mixture proved the formation of the water-soluble conjugate at a yield of not less than 95%.

The conjugate was dialyzed against DDW for 30 hours at 4° C. using SPECTRA/POR molecular porous membrane tubing with a M.W. cutoff of 12–14 Kd, followed by centrifugation for 10 mins. at 2,000 rpm and lyophilization.

925 mg of the lyophilized final product was obtained, comprising 65% polymer as determined by the anthrone method and 35% Nys as evaluated by UV absorption at 419–420 nm. The yield of Nys in the conjugate was 87% and the calculated yield of the polymer was 67%.

The lyophilized conjugate is readily dissolved in water at concentrations as high as 100 mg/ml, while free Nys is easily dissolved only in DMSO at a concentration of 30 mg/ml or higher, less in methanol (1 mg/ml) and very slightly in water (0.2–0.4 mg/ml). In contrast, the Nys-dextran conjugates are not soluble in DMSO or methanol.

UV spectra of the conjugates are similar to that of free Nys, but its coupling with DAD leads to certain shifts in peak wavelengths as follows (wavelengths in nm):
Nys in DMSO: 415–416, 391–396, 320–324, 305–309, 292, 295;
solutions of Nys in mixtures of DMSO-water: 416–418, 392–395, 321–323, 306–308, 289–291;
conjugates in aqueous solutions:
  unreduced form: 417–419, 392–393, 321, 306–307, 289–293, 270–273, 231;
  reduced form: 419–420, 394, 322, 307, 285–289, 271–275, 232–233.

The coupling process was studied as a function of molecular weight and degree of oxidation of dextran, drug-polymer ratio, pH, temperature and reaction time. Dextrans with a molecular weight range of 9,300–74,000 and a degree of oxidation of 5–50% were reacted with Nystatin in aqueous buffer solutions of pH ranging between 7.5–10 at 4°–37° C. for 2–20 hours. Drug and polymer concentrations in the reaction mixture ranged from 5–15 mg/ml and from 5–50 mg/ml, respectively. The results are presented in Table 1.

TABLE 1

| No | MW-1 | Ox | pH | TI | TP | MW-2 | DD | NY | Y |
|----|------|----|----|----|----|------|----|----|---|
| 1 | 9300 | 10 | 7.0 | 2 | 20 | 9000 | 35 | 5 | 3 |
| 2 | 9300 | 50 | 8.9 | 16 | 37 | 6000 | 20 | 10 | 90 |
| 3 | 18000 | 5 | 7.5 | 6 | 4 | 18000 | 20 | 10 | 5 |
| 4 | 18000 | 12 | 8.0 | 24 | 20 | 15000 | 35 | 15 | 20 |
| 5 | 18000 | 25 | 8.5 | 16 | 37 | 12000 | 20 | 10 | 50 |
| 6 | 18000 | 50 | 8.9 | 16 | 37 | 9000 | 35 | 10 | 95 |
| 7 | 18000 | 12 | 9.5 | 2 | 4 | 6000 | 20 | 20 | 70 |
| 8 | 18000 | 12 | 10.0 | 2 | 4 | 5300 | 10 | 20 | 40 |
| 9 | 40000 | 25 | 9.5 | 2 | 4 | 15000 | 35 | 20 | 70 |
| 10 | 40000 | 50 | 8.5 | 10 | 20 | 20000 | 10 | 10 | 50 |
| 11 | 40000 | 50 | 8.9 | 20 | 37 | 14000 | 25 | 10 | 95 |
| 12 | 74000 | 25 | 10.0 | 4 | 4 | 13000 | 25 | 15 | 60 |
| 13 | 74000 | 50 | 8.9 | 16 | 37 | 20000 | 25 | 5 | 95 |

No. - experiment no.
MW-1 - dextran M.W.
Ox - degree of oxidation
MW-2 - DAD M.W.
pH,TI,TP - pH, time (hours) and temperature (°C.) of reaction
DD,NY - DAD and Nys concentrations in product (mg/ml)
Y - Nys yield (%)

Reducing the pH of the reaction mixture leads to a lower product yield, while pH values over 9.0 lead to drastic polymer degradation and Nystatin inactivation. Furthermore, a decrease in the extent of polymer oxidation results in lower degradability of the polymer, but at the same time also leads to lower Nys binding.

Figure 3:
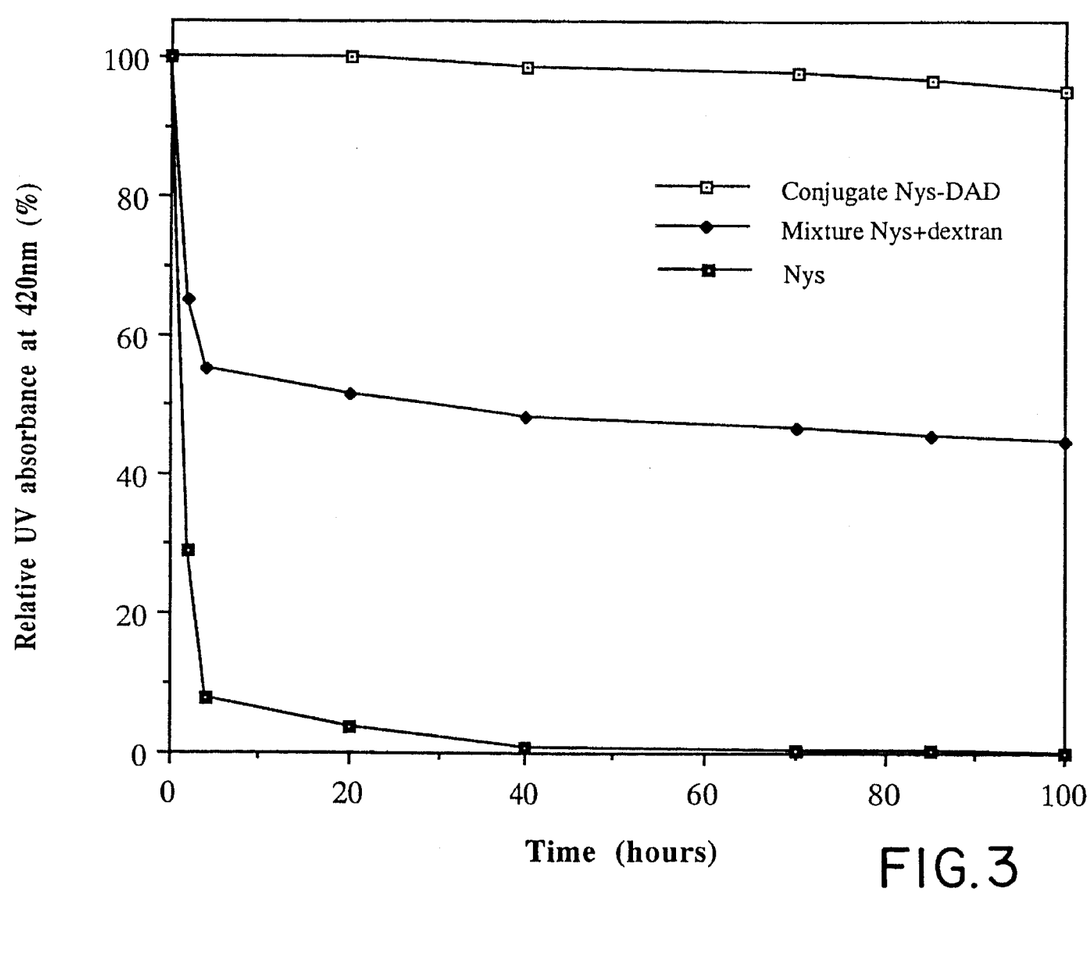
FIG. 3 illustrates the results of a stability experiment measured as a function of time.

The stability of the conjugate in aqueous solution was compared to that of free Nys and to a mixture of Nys and dextran at 37° C. As illustrated in FIG. 3, the conjugate almost completely retained its UV absorbance for more than 100 hours as opposed to the other preparations which were rapidly degraded.

Figure 5:
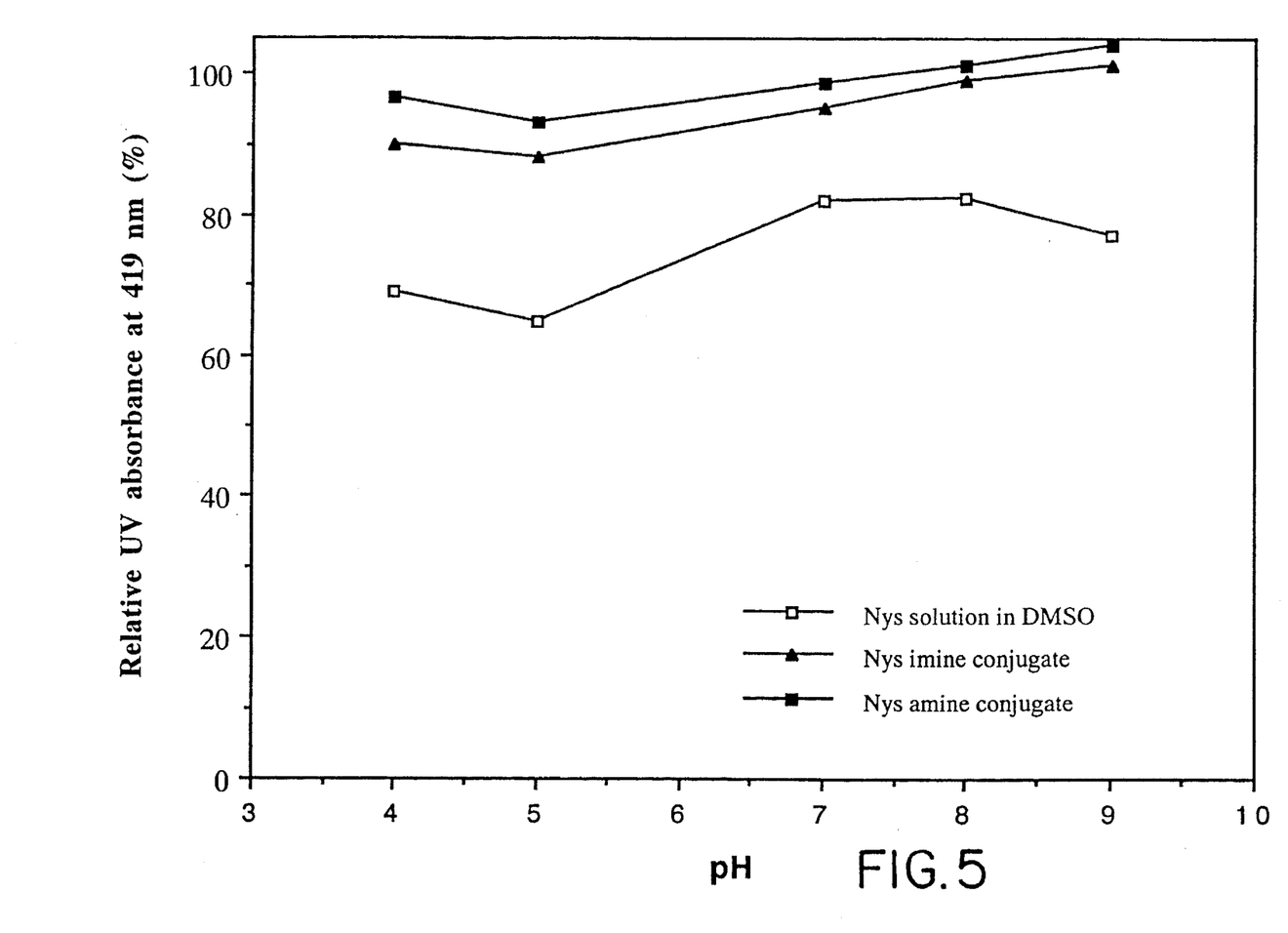
FIG. 5 illustrates the results of a stability experiment measured as a function of pH.

FIG. 5 illustrates the increased pH stability of the unreduced conjugate in aqueous solution as opposed to free Nys in DMSO. The preparations were incubated at room temperature for a period of 20 hours in phosphate-buffered solutions of various pH's.

The above results support the conclusion that coupling of a polyene antibiotic to a polysaccharide according to the method of the invention markedly increases the water-solubility and stability of the polyene drug.

Figure 6A:
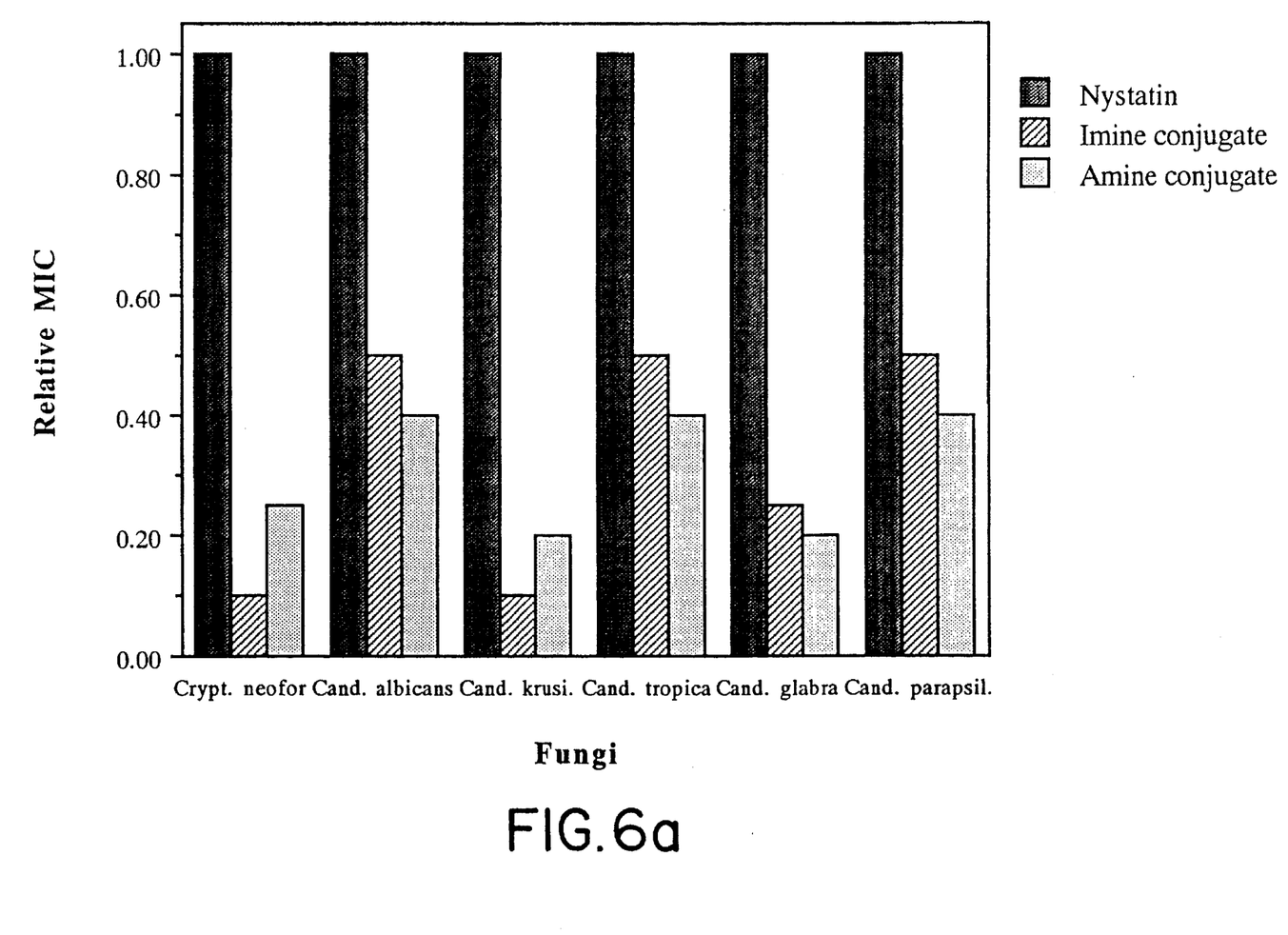
FIGS. 6a and 6b demonstrate the efficacy of the conjugates of the invention as measured in an in vitro assay 24 (FIG. 6a) and 48 (FIG. 6b) hours after fungi inoculation.
Figure 6B:
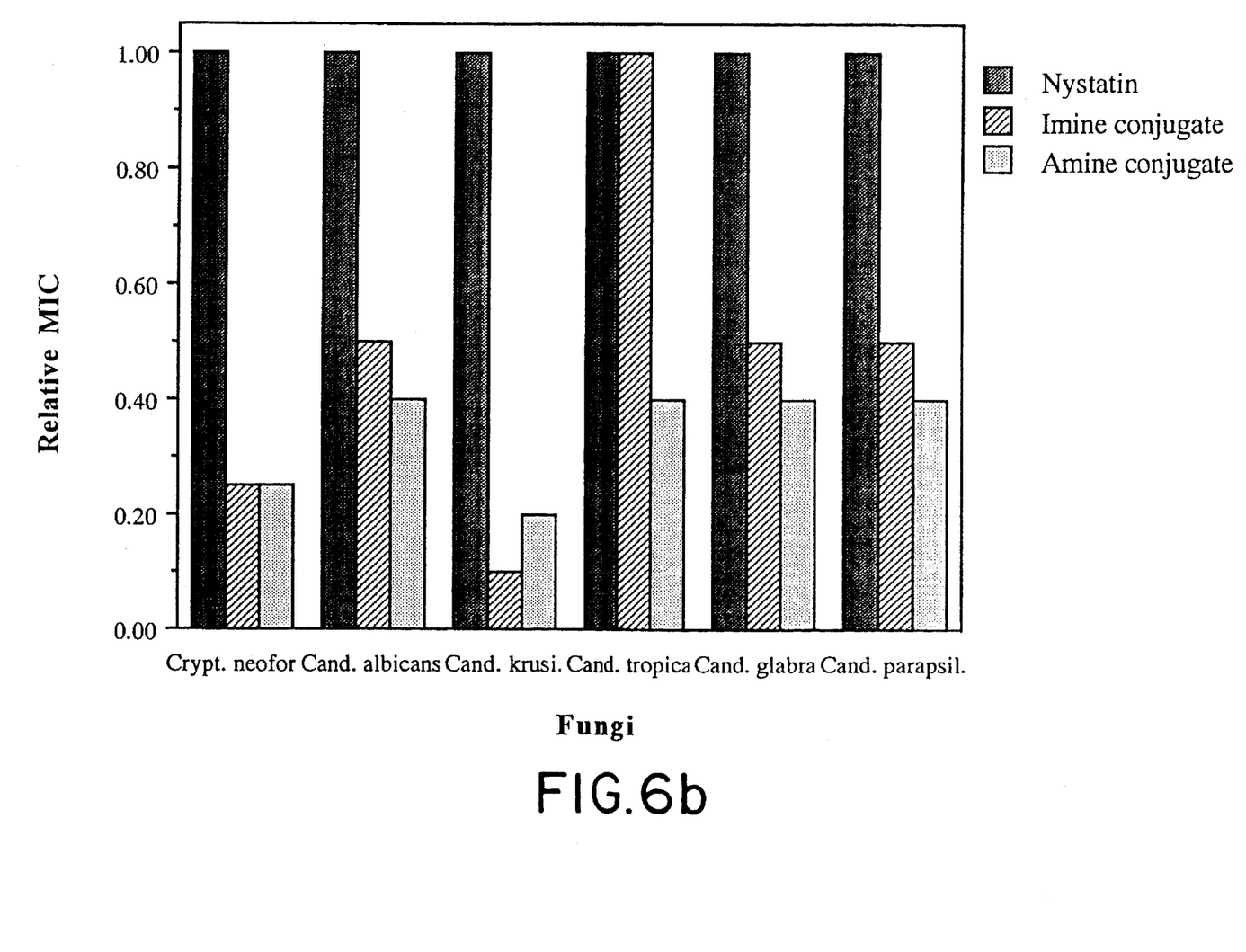

The antifungal efficacy of the unreduced conjugate (#3) was tested in an MIC test, relative to free Nys (#1), with respect to various fungi (FIGS. 6a and 6b). The conjugate was shown to be more than twice as effective (lower MIC values) as the free drug. Similar results were obtained for arabinogalactan conjugates of Nys and Amph B (not shown).

Figure 7:
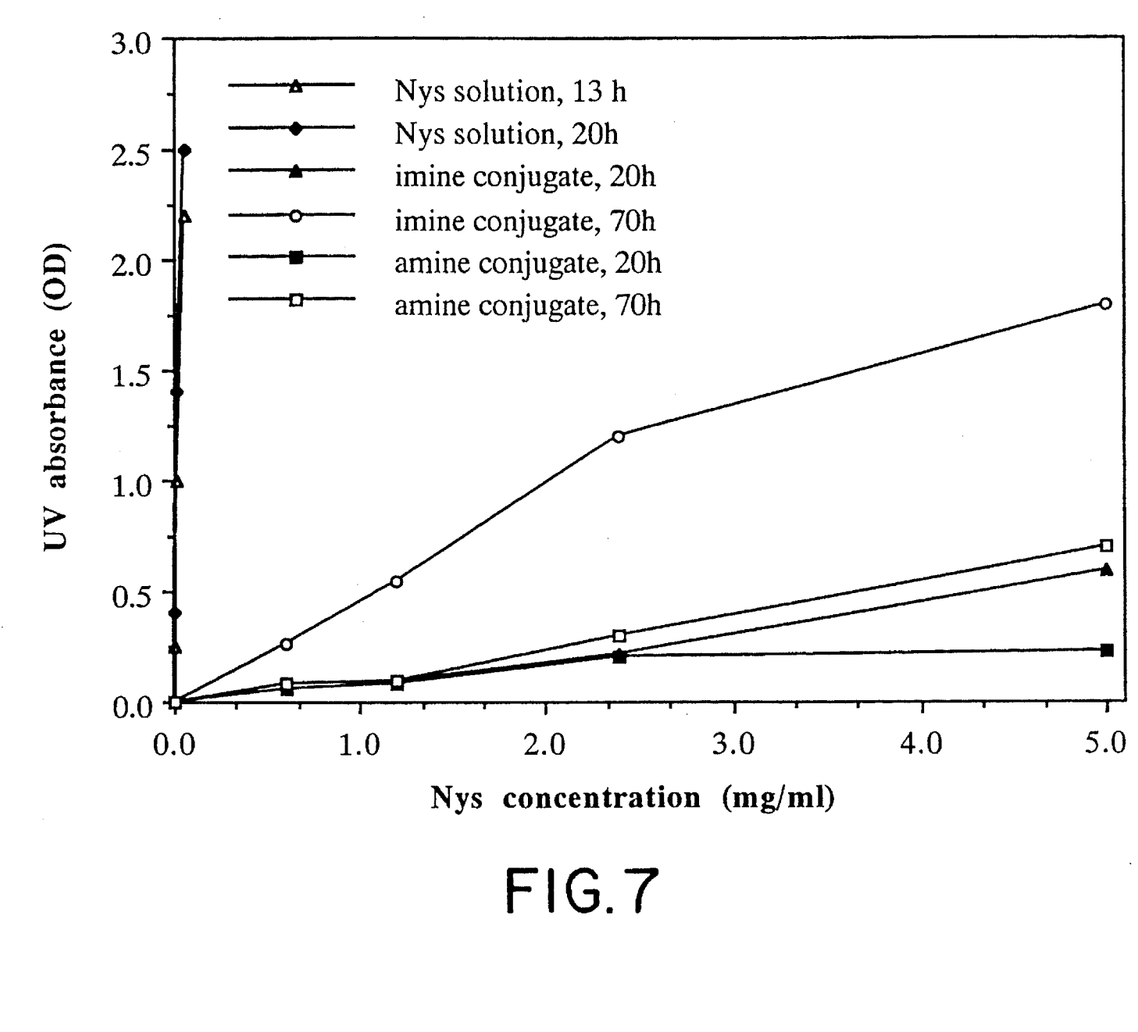
FIG. 7 illustrates an in vitro toxicity study of the conjugates of the invention.

The sterile unreduced (imine) conjugate preparations were much less toxic than the free drug as measured in an in vitro assay (FIG. 7). The comparative evaluation of acute toxicity values for Nys and the unreduced conjugate in an in vivo toxicity test showed that while the maximal tolerated dose (MTD) for a single injection of drug was 3–4 mg/kg for Nys, the value was >700 mg/kg for the conjugate.

Example 2—Formation of Amine Conjugate

The Nys-dextran conjugate was obtained as described in Example 1. However, after conjugation the reaction mixture was treated with a double molar excess of sodium borohydride at 4° C. for 30 mins. All of the subsequent procedures were then carried out as described in Example 1 above. The resulting conjugate (945 mg) comprised 66% polymer as determined by the anthrone method and 34% coupled Nys as evaluated by UV absorption at 419–420 nm. The yield of Nys in the conjugate was 86% and the calculated yield of the polymer was 69%.

Figure 4:
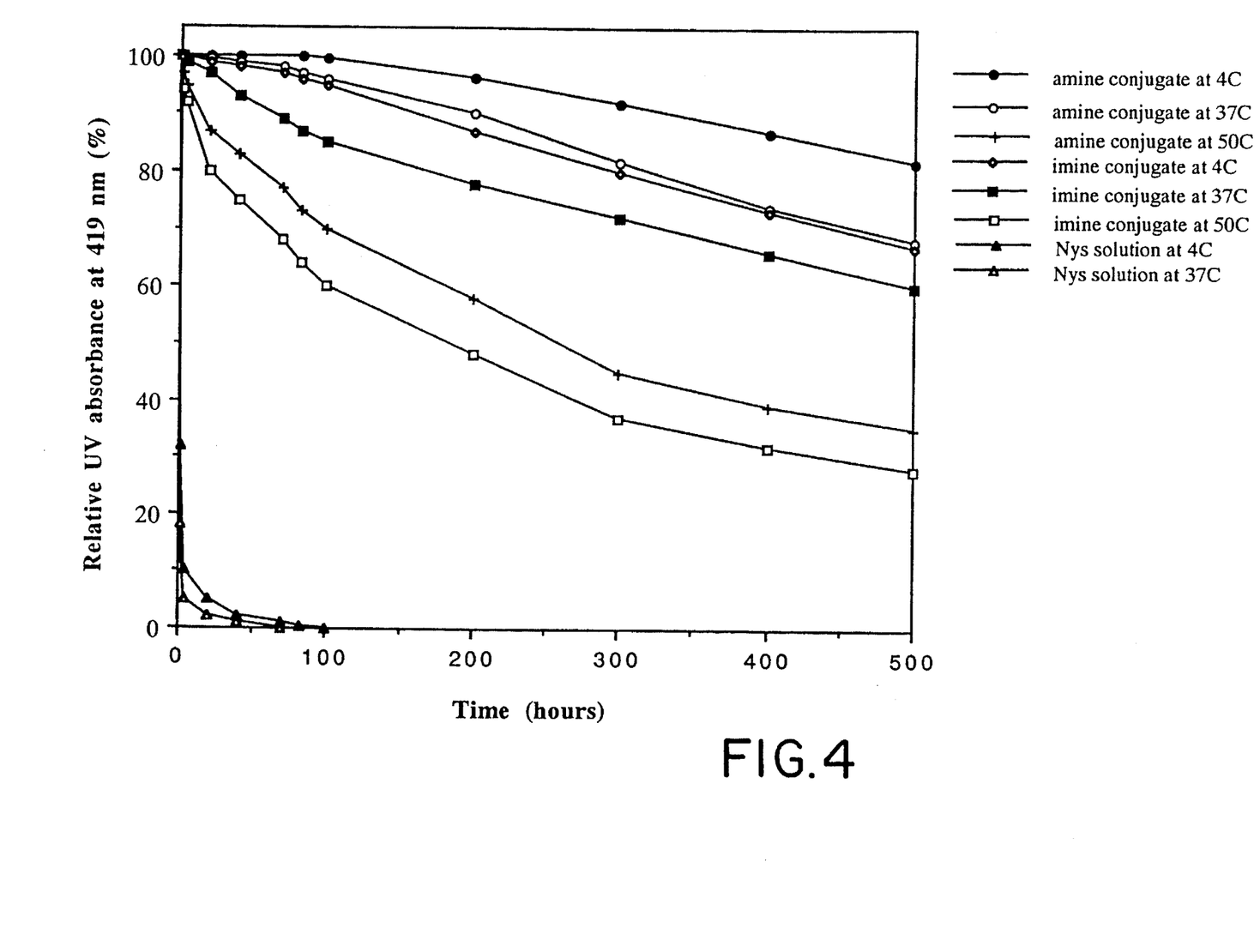
FIG. 4 illustrates the results of a stability experiment measured as a function of temperature and time.

The reduced conjugate was lighter in color than its unreduced counterpart, and had a higher water solubility (up to 200 mg/ml). A 1 mg/ml aqueous solution of the reduced (amine) conjugate was found to be significantly more stable than an equivalent solution of the unreduced (imine) form as measured over a period of 500 hours at 4° C., 37° C. and 50° C. (FIG. 4). The pH stability of the reduced conjugate was also found to be slightly superior to that of the unreduced conjugate (FIG. 5).

The reduced preparation (#2) had activity in MIC tests similar to the unreduced conjugate (#3) (FIGS. 6a and 6b). In vitro toxicity studies (FIG. 7) showed that the amine derivative was much less toxic than the free drug, and significantly less toxic than the imine derivative. In the in vivo toxicity studies described in example 1, the MTD for the reduced conjugate was 880 mg/ml. In a second experiment in which mice were injected daily for five consecutive days, the MTD for the conjugate was 150 mg Nys/kg/day as compared to 1 mg Nys/kg/day for free Nys.

Figure 8:
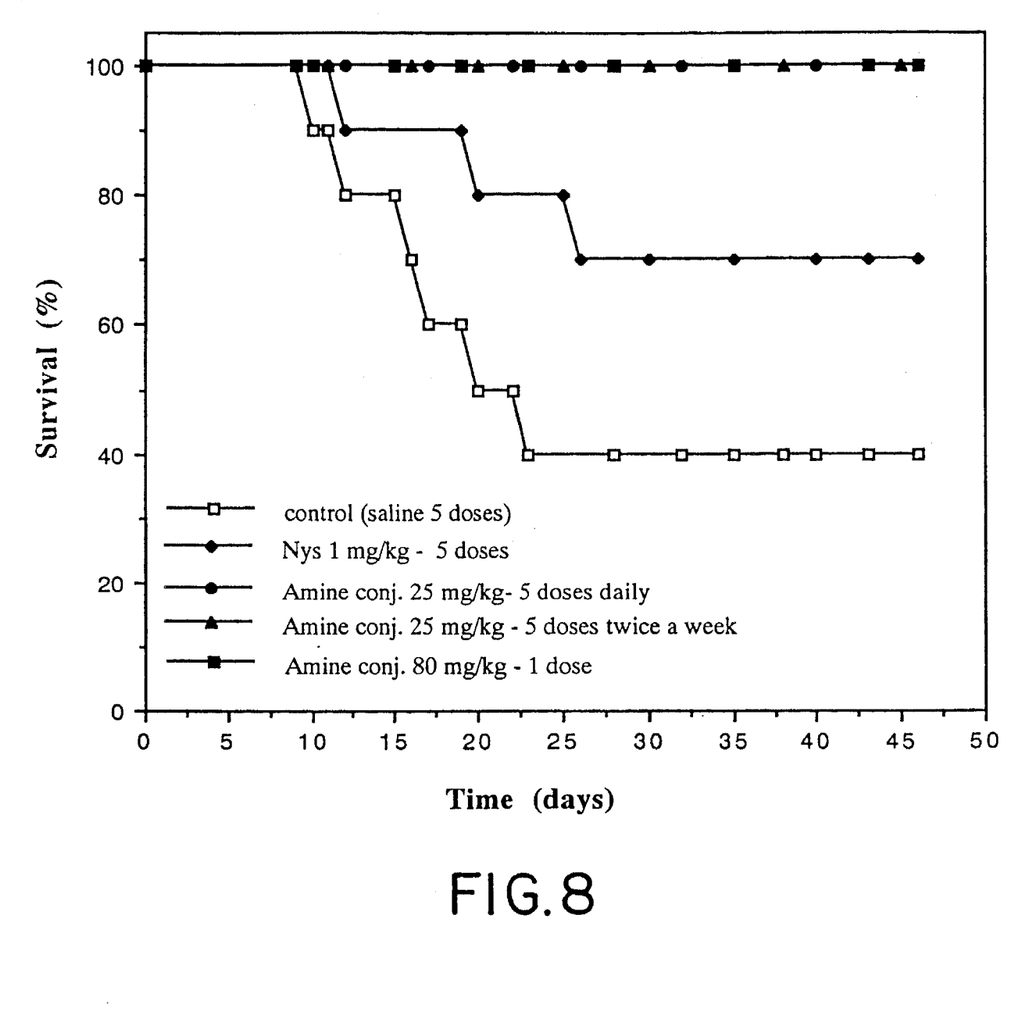
FIG. 8 demonstrates the efficacy of the conjugates of the invention as measured in an in vivo assay after inoculation with a low concentration of murine candidiasis cells.
Figure 9:
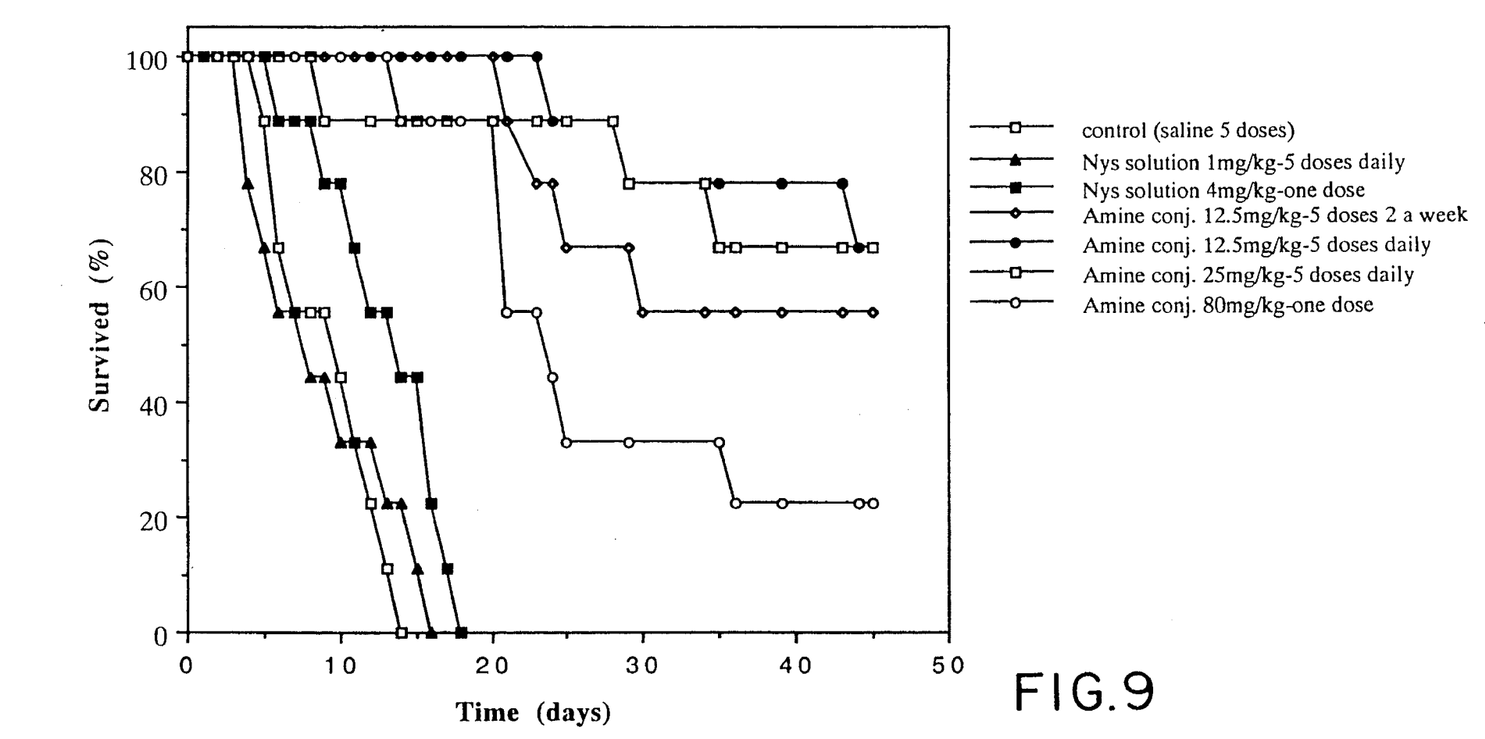
FIG. 9 demonstrates the efficacy of the conjugates of the invention as measured in an in vivo assay after inoculation with a high concentration of murine candidiasis cells.
Figure 10A:
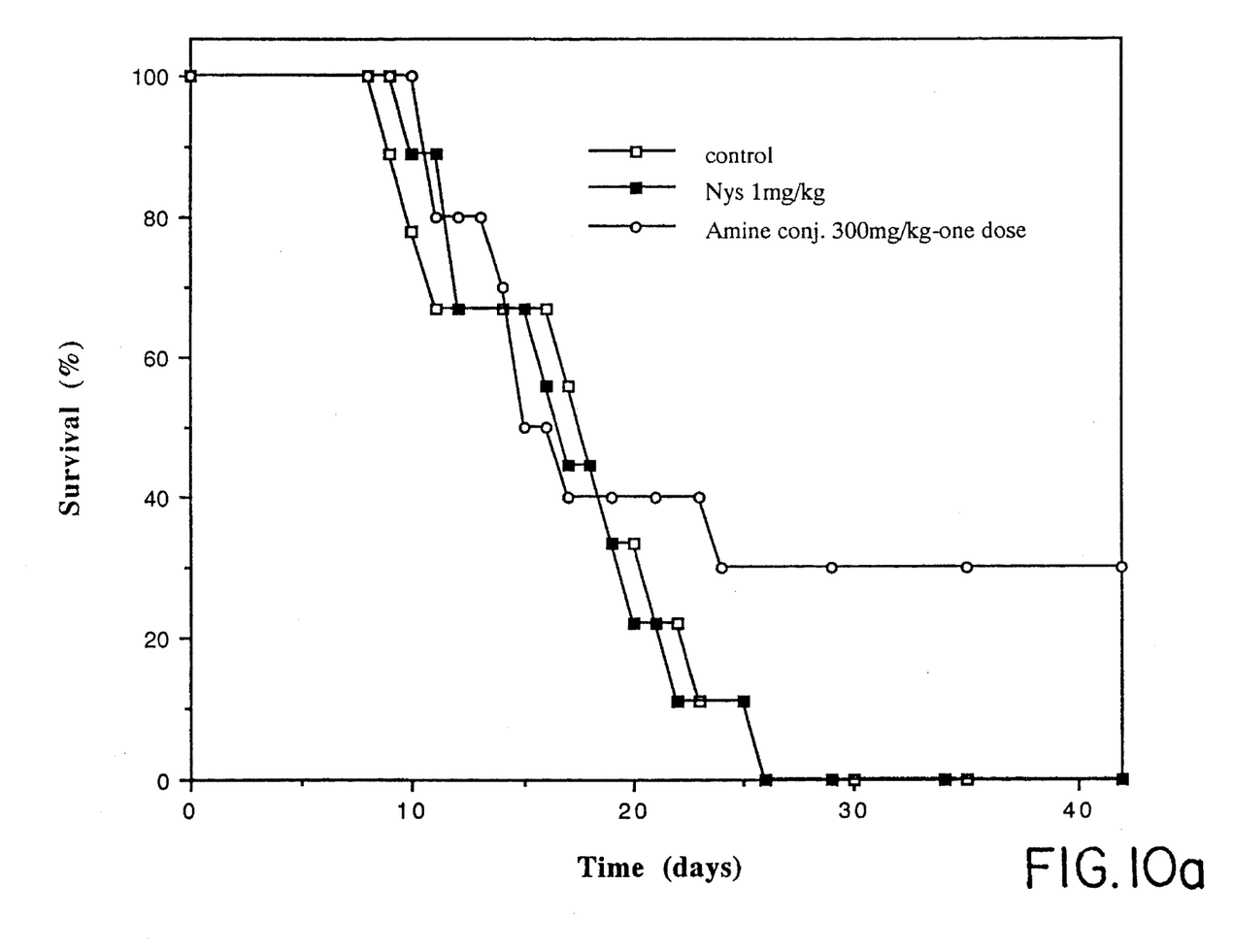
FIGS. 10a and 10b demonstrate the efficacy of the conjugates of the invention as measured in an in vivo assay after a single (FIG. 10a) or multiple (FIG. 10b) inoculation with a low concentration of murine cryptococcosis cells.
Figure 10B:
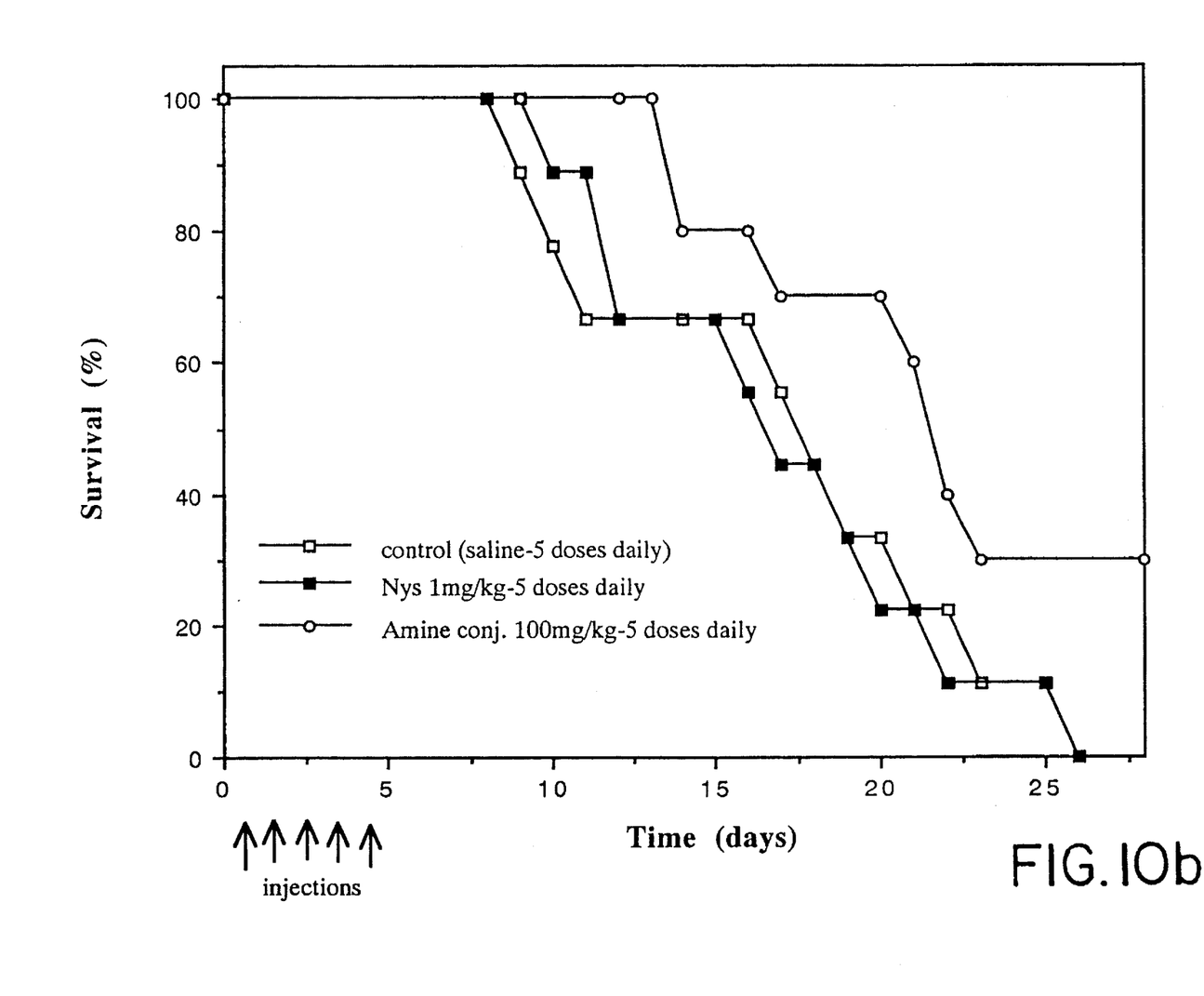

In vivo efficacy tests were also carried out, as illustrated in FIGS. 8–10, to compare the reduced conjugate to free Nys.

FIG. 8 illustrates the results of an experiment in which $3 \times 10^3$ C. albicans cells/0.2 ml. were injected into mice prior to treatment with the drug or drug-conjugate, as indicated in the figure. FIGS. 10a and 10b illustrate similar experiments with $2 \times 10^3$ cells of murine crypt. neoformans. FIG. 9 illustrates the results of an experiment in which $10^5$ C. albicans cells/0.2 ml were injected into the mice. All of the in vivo experiments clearly show the increased antifungal effectiveness of the conjugate as compared to the free drug.

Example 3

The conjugate was prepared as described in Example 2, except that 9,300 MW dextran was used, and the final dextran concentration in the reaction mixture was 20 mg/ml. To prevent the conjugate from passing through the dialysis tubing, SPECTRA/POR molecular porous membrane tubing with a M.W. cutoff of 6,000 was used. The resulting conjugate weighing 940 mg contained 36% of the coupled Nys, and the final yield was 91% for Nys and 67% for the polymer. The MIC and toxicity results of the conjugate were similar to those of the conjugate of example 2 (not shown).

Example 4

The conjugate was prepared as described in Example 2, except that 74,000 MW dextran was used, and the initial concentration of Nys was 5 mg/ml. When the product was applied to a Sephadex G-75 column, two peaks were observed corresponding to conjugates having various molecular-weights.

Example 5

The conjugate was prepared as described in Example 2, except that the soluble polysaccharide arabinogalactan (Larex UF)—a polymer of arabinose and galactose (1:6)—was used instead of dextran. The initial concentrations of the oxidized polymer and Nys were 25 mg/ml and 3 mg/ml, respectively. The yield of drug in the polymeric conjugate was 80%.

Example 6

A conjugate of Amph B and arabinogalactan was prepared under the conditions described in example 2. The initial concentrations of the oxidized polymer and drug were 20 mg/ml and 5 mg/ml, respectively. The yield of drug in the polymeric conjugate was 75%.

Example 7

Fungizone (soluble Amph B) was conjugated to arabinogalactan under the conditions of example 2. The initial concentrations of the oxidized polymer and Amph B were 20 mg/ml and 10 mg/ml, respectively. The yield of drug in the polymeric conjugate was 95%.

Example 8

In order to compare the conjugation method of the invention to that of GB 978,170, 3 Nys-dextran conjugates were prepared: (1) Nys (10 mg/ml) was conjugated to unpurified DAD (20 mg/ml) for 20 min. at 50° C. in a strong alkaline medium of 1M NaOH (the pH of the reaction mixture decreased from 13.5 to 12.5 over the course of the reaction; (2) Nys was conjugated to unpurified DAD for 10 hours at 37° C. in 0.1M borate buffer (pH 8.8–9.0); (3) as in (2) except that carefully purified DAD (oxidative anion content <2.5%) was used in accordance with the method of the invention.

Although both conjugates #1 and #2 dissolved rapidly in water, the solutions, as well as their extremely hygroscopic lyophilizates, contained a mixture of two main fractions as measured by GPC—a minor peak corresponding to a polymeric conjugate and a major peak corresponding to a low-molecular-weight product eluting with the total volume of the chromatographic column. In both fractions, the Nys was significantly inactivated, as evidenced by the complete disappearance of the 419 nm and 393 nm UV peaks, and the remaining antifungal activity was found not to exceed 8%. This is in marked contrast to conjugate #3 in which the two aforementioned UV peaks were of the same magnitude as in the free drug, and only a high-molecular-weight fraction was present in the HPLC elution.

The alcove results clearly show that both the preliminary purification of the DAD as well as the maintenance of the pH of the reaction mixture at no higher than 9.0 are required in order to obtain a stable, active Nys-conjugate preparation.

While the present invention has been described in terms of several preferred embodiments, it is expected that various modifications and improvements will occur to those skilled in the art upon consideration of this disclosure.

The scope of the invention is not to be construed as limited by the illustrative embodiments set forth herein, but is to be determined in accordance with the appended claims.

REFERENCES

1. Mehta, R. T., Lopez-Bernstein, G. et al., 1984, BBA, 770, 230–234.

2. Maddux, M. S. & Barriere, S. L., 1980, *Drug Intel. Clin. Pharm.*, 14, 177–181, or Richardson, S. E., Bannatyre, R. M. et al., 1988, *Rev. Infect. Dis.*, 10, 1171–1181.
3. Mehta, R. T., Lopez-Bernstein, G. 1987, *Antimicrob. Agents Chemother.*, 321, 1897–1900.
4. De Gregorio, M. W., Lee, W. M. F. & Reis, C. A., 1982, *Cancer*, 50, 2780–2784.
5. Larsen, C., 1990, in *Dextran Prodrugs. Physico-chemical and chemical aspects in relation to in vivo properties*, Arhus. Odense. 233p.
6. Levy-Schaffer, F., Bernstein, A., et al., 1982, *Cancer Treat. Rep.*, 666, 107–114.
7. Bernstein, A., Hurwitz, E., et al., 1978, *J. Nat. Cancer Inst.*, 60, 379–384.
8. Law, S., Lo, W., & Teh, G., 1988, *Drug. Dev. Ind. Pharm.*, 14, 143–153.
9. Rogovin, Z., Vyrnik, A., Khomyakov, K. et al., 1972, *Vysokomol.soed.*, 7, 1035–1040.
10. Hurwitz, E., et.al., 1980, J. Appl. Biochem., 2, 25–35.
11. Polacheck, I., Zehavi, U., Levy, M., et al., 1986, *Antimicrob Agents Chemother.*, 30, 290–294.
12. Lindenbaum, G. (Linden), Mirgorodskaya, O., & Moskvichev, B., 1977, *Khim-Pharm. J.*, 11, #6, 80–83.
13. Chazov, E., Smirnov, V. et al., 1984, F.R.G. Patent DE 3,032,606.
14. Chazov, E., Smirnov, V., et al., 1984, U.S. Pat. No. 4,446,316.
15. Lindenbaum, G. M., Yakovleva, M. F., et al., 1982, Prikl. Biochim. Mikrobiol., 18, #2, 212–220.
16. Michel, G., 1977, *Analytical Profiles of Drug Substances* (ed. Florey K.), 6, 341–421.

We claim:

1. A substantially stable water-soluble conjugate of a polysaccharide and an unoxidized, biologically-active polyene antibiotic, said antibiotic being conjugated to said polysaccharide via an imine bond.

2. A conjugate according to claim 1 wherein said antibiotic is nystatin.

3. A substantially stable water-soluble conjugate of a polysaccharide and an unoxidized, biologically-active polyene antibiotic, said antibiotic being conjugated to said polysaccharide via an amine bond.

4. A conjugate according to claim 3 wherein said antibiotic is nystatin.

5. A method for producing a substantially stable water-soluble polysaccharide conjugate of a polyene antibiotic comprising:

(a) activating said polysaccharide to a dialdehyde by periodate oxidation;

(b) purifying said dialdehyde from interfering anions and by-products;

(c) coupling said antibiotic to said purified dialdehyde by Schiff base formation to form said conjugate; and (d) purifying said conjugate.

6. A method according to claim 5 further comprising, following step (c), the step of:

reducing said conjugate to an amine conjugate by a reducing agent.

7. A method according to claim 6 wherein said reducing agent is selected from the group consisting of $NaBH_4$, $NaHSO_3$, and $HO—NH_2HCl$.

8. A method according to claim 7 wherein said reducing agent is $NaBH_4$.

9. A substantially stable water-soluble polysaccharide amine conjugate of a polyene antibiotic prepared according to the method of claim 6.

10. A conjugate according to claim 9 which is Nystatin-dextran.

11. A method according to claim 5 wherein said antibiotic is Nystatin.

12. A method according to claim 5 wherein said antibiotic is amphotericin B.

13. A method according to claim 5 wherein said polysaccharide is dextran.

14. A method according to claim 13 wherein said dextran has a molecular weight of between 9000 and 75,000 dalton.

15. A method according to claim 5 wherein said polysaccharide is arabinogalactan.

16. A method according to claim 5 wherein said dialdehyde is purified by applying it to a strongly basic anion exchanger.

17. A substantially stable water-soluble polysaccharide imine conjugate of a polyene antibiotic prepared according to the method of claim 5.

18. A conjugate according to claim 17 which is Nystatin-dextran.

19. A pharmaceutical composition for use in the treatment of fungal infections comprising the conjugate of claim 17.

20. A pharmaceutical composition according to claim 19 suitable for intravenous administration.

* * * * *